(12) United States Patent
Guo et al.

(10) Patent No.: US 7,081,106 B1
(45) Date of Patent: Jul. 25, 2006

(54) HEMOSTASIS VALVE

(75) Inventors: Xiaoping Guo, Bloomington, MN (US); Richard Stehr, Stillwater, MN (US)

(73) Assignee: St. Jude Medical, Atrial Fibrillation Division, Inc., Maple Grove, MN (US)

( * ) Notice: Subject to any disclaimer, the term of this patent is extended or adjusted under 35 U.S.C. 154(b) by 0 days.

(21) Appl. No.: 10/417,665

(22) Filed: Apr. 17, 2003

Related U.S. Application Data

(62) Division of application No. 09/491,221, filed on Jan. 25, 2000, now Pat. No. 6,551,283.

(51) Int. Cl.
*A61M 5/178* (2006.01)

(52) U.S. Cl. ............... 604/167.06; 251/149.1; 604/167.04; 604/256

(58) Field of Classification Search ........... 604/167.01, 604/167.02, 167.03, 167.04, 167.06, 237, 604/247, 264; 251/149.1, 149.2
See application file for complete search history.

(56) References Cited

U.S. PATENT DOCUMENTS

| | | | |
|---|---|---|---|
| 2,023,267 A | 12/1935 | De Saint Rapt et al. | |
| 4,000,739 A | 1/1977 | Stevens | |
| 4,430,081 A | 2/1984 | Timmermans | |
| 4,610,655 A | 9/1986 | Müller | |
| 4,626,245 A | 12/1986 | Weinstein | |
| 4,629,450 A | 12/1986 | Suzuki et al. | |
| 4,655,752 A | 4/1987 | Honkanen et al. | |
| 4,673,393 A | 6/1987 | Suzuki et al. | |
| 4,705,511 A | 11/1987 | Kocak | |
| 4,798,594 A | 1/1989 | Hillstead | |
| 4,895,346 A | 1/1990 | Steigerwald | |
| 4,895,565 A | 1/1990 | Hillstead | |
| 4,909,798 A | 3/1990 | Fleischhacker et al. | |
| 4,917,668 A | 4/1990 | Haindl | |
| 5,000,745 A | 3/1991 | Guest et al. | |
| 5,041,095 A | 8/1991 | Littrell | |
| 5,114,408 A | 5/1992 | Fleischhaker et al. | |
| 5,125,903 A | 6/1992 | McLaughlin et al. | |
| 5,149,327 A | 9/1992 | Oshiyama | |
| 5,154,701 A | 10/1992 | Cheer et al. | |
| 5,167,637 A | 12/1992 | Okada et al. | |
| 5,176,652 A | 1/1993 | Littrell | |
| 5,207,656 A | 5/1993 | Kranys | |
| 5,520,655 A | 5/1996 | Davila et al. | |
| 5,643,227 A | 7/1997 | Stevens | |
| 5,779,697 A | 7/1998 | Glowa et al. | |
| 6,024,729 A | 2/2000 | Dehdashtian et al. | |
| 6,149,632 A | 11/2000 | Landuyt | |
| 6,277,100 B1 * | 8/2001 | Raulerson et al. | 604/212 |
| 6,551,283 B1 * | 4/2003 | Guo et al. | 604/167.06 |
| 6,632,200 B1 * | 10/2003 | Guo et al. | 604/247 |

* cited by examiner

*Primary Examiner*—Kevin C. Sirmons
(74) *Attorney, Agent, or Firm*—Scott R. Cox

(57) ABSTRACT

A hemostasis cannula unit including a valve housing, a cap, and a hemostasis valve, wherein the hemostasis valve includes a valve gasket and a valve membrane compressed against the valve gasket by the valve housing, wherein the valve gasket is thicker than the valve membrane.

28 Claims, 5 Drawing Sheets

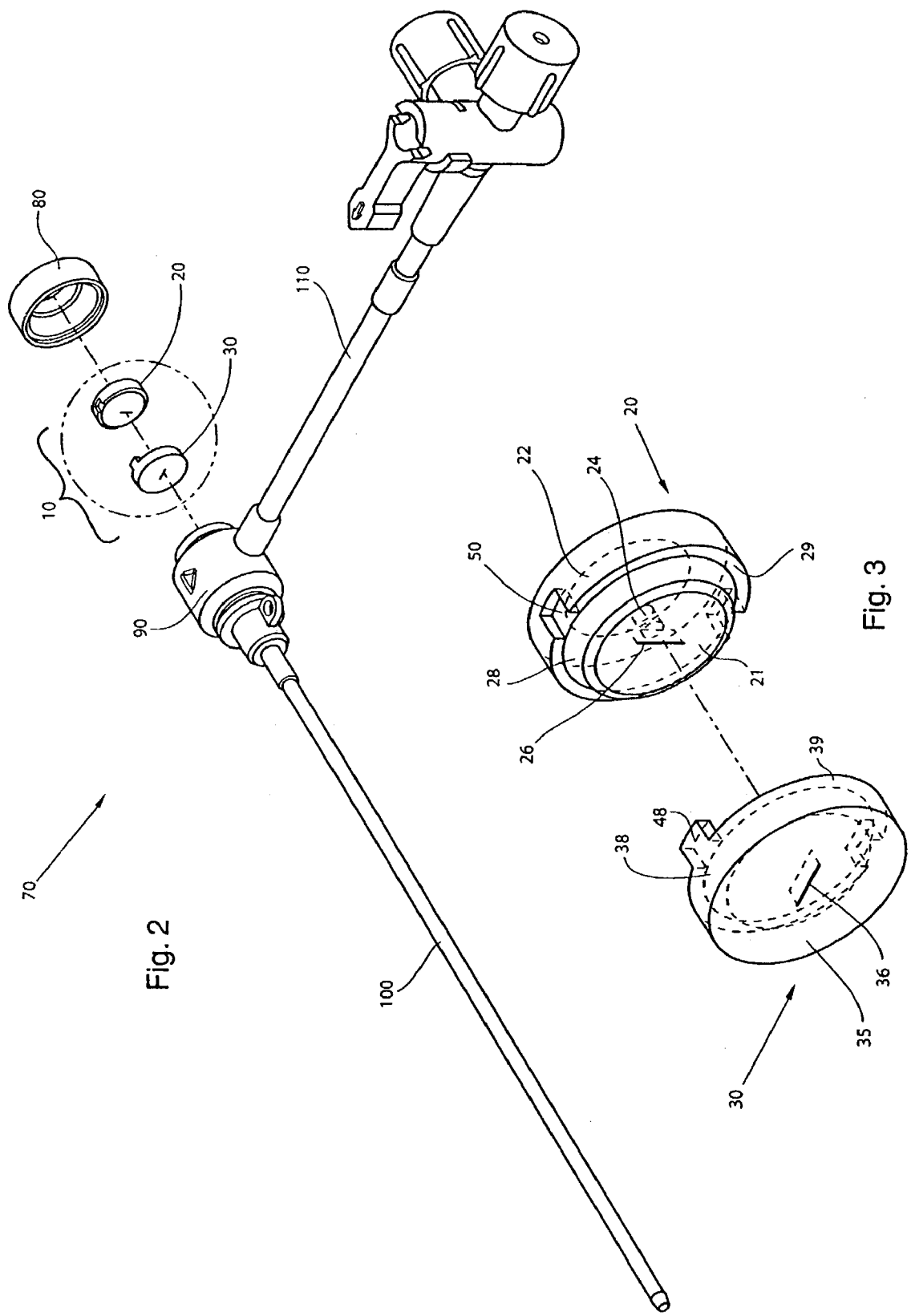

HEMOSTASIS VALVE

CROSS-REFERENCE TO RELATED APPLICATIONS

This application is a divisional of application Ser. No. 09/491,221 filed on Jan. 25, 2000, now U.S. Pat. No. 6,551,283.

BACKGROUND OF INVENTION

1. Field of Invention

This invention relates to medical devices and instruments. More particularly, this invention relates to hemostasis valves and hemostasis cannula units containing a hemostasis valve, wherein the hemostasis valve is comprised of two separate valve members, a valve gasket and a complementarily shaped valve membrane, each of which has a different thickness.

2. Prior Art

The introduction of catheters into blood vessels for a variety of purposes such as coronary angiography has been known for many years. Several techniques for introducing these catheters into the vasculature of the human body are available. One such technique is the cut-down method, while another is the Seldinger technique. The Seldinger technique includes surgically opening a vein or artery with a needle, inserting a guidewire into the vessel through the lumen of the needle, withdrawing the needle, inserting over the guidewire a dilator which has passed through an associated sheath containing a hemostasis valve, removing the dilator and inserting a catheter through the hemostasis valve and sheath into the blood vessel.

A wide variety of hemostasis valves are known in the prior art. However, when a guidewire is inserted through most hemostasis valves, because the guidewire is so small relative to the catheters which may also be employed, it is difficult for the valve to seal adequately against the backward pressure of blood, while at the same time permitting easy insertion of much larger diameter catheters into the vasculature. This problem is particularly acute with catheterization procedures involving arterial invasion where there is a high reverse pressure of blood. In these arterial procedures, blood can squirt out when the guidewire is introduced through the hemostasis valve. Excessive blood leakage may be extremely dangerous to patients and a contaminant to physicians. Accordingly, most prior art hemostasis valves are designed for use with only one particular size of catheter. It has often been difficult to employ a single hemostasis valve with catheters of widely varying diameters because adequate sealing around the catheter walls cannot be achieved.

Cardiac catheter introducers used during coronary procedures often contain a hemostasis valve that is mounted in the valve housing or hub secured on the proximal end of the introducer. Such an introducer is conventionally used to facilitate the insertion of the catheters and guidewires into the vascular system of a patient, while minimizing injury to the patient at the access site and improving the patient's comfort during the cardiac catheterization procedure. An introducer is particularly necessary where one or more treating catheters of varying diameters are inserted into and removed from the patient's vessel repeatedly as occurs in angiographic procedures and angioplasty. The presence of the catheter introducer and the insertion of different size catheters often causes bleeding during cardiac catheterization procedures. A high performance hemostasis valve is therefore needed to seal against the leakage of blood out of or around catheters and guidewires having varying diameters as they enter an artery or other blood vessel. The hemostasis valve must also prevent the reverse seepage of air into the artery or blood vessel of the patient when one or more than one of the elongated catheters or guidewires are withdrawn from the introducer. In addition, the valve must remain sealed when there is no medical device passing through the valve. Accordingly, the requirements for a useful hemostasis valve include at least the following: (a) the valve is always sealed when no elongated cylindrical member is introduced into it; (b) the insertion and retraction forces must be minimal when larger diameter catheters (such as those larger than about 9 F (3 mm)) are introduced into the valve; (3) in contrast, the valve must maintain good sealability when small diameter guidewires (such as those down to 0.014 in. (0.35 mm)) pass through its passageway; and (4) to the greatest extent possible, the deformation of the valve must be in a radial direction instead of an axial direction to prevent the transmission of air into the blood stream.

Numerous hemostasis valves are known which can be classified in three major groups. Type I, as disclosed, for example, in U.S. Pat. Nos. 5,041,095 and 5,176,652, contain a pair of gaskets of approximately equal thickness. Each gasket has a Y-shaped opening cut into the gasket radially extending from its center forming three (3) slits, each located at an angle of about 120 degrees from the other slits. Each slit penetrates the gasket from one end face to the other end face. To form a self-sealing hemostasis valve, the two Y-shaped slits of the respective gaskets are mounted in a position opposite to one another in the valve housing.

Other types of hemostasis valves containing multiple disks which are approximately the same size and thickness are disclosed, for example, in U.S. Pat. Nos. 2,023,267; 4,000,739; 4,430,081; 4,655,752; 4,673,393; 4,895,346; 5,000,745; and 5,643,227. Each of these patents discloses a different combination of valve disks that are used to form the hemostasis valve. In some embodiments, one of the disks contains Y-shaped slits and the other disk contains a circular opening in the center of that disk.

Type II hemostasis valves as disclosed in U.S. Pat. Nos. 4,626,245; 4,629,450; 5,114,408; 5,149,327 and 5,167,637 and utilize a single sealing disk. The disk generally has a first slit that opens at only one end face and a second slit that opens at only the other end face. The two slits, which form a crisscross, intersect each other inside the disk. Other types of single sealing disk hemostasis valves with different shapes for the opening through that disk are disclosed, for example, in U.S. Pat. Nos. 4,705,511 (see FIG. 4); U.S. Pat. No. 4,798,594 and 4,895,565.

Type III hemostasis valves, as disclosed, for example, in U.S. Pat. Nos. 5,149,327; 5,207,656 and 5,520,655, are similar to Type II hemostasis valves, but differ in that only one slit (Y-shaped or +-shaped) penetrates from one end face to the other end face of the gasket.

Other types of hemostasis valves can be found in various patents such as in U.S. Pat. Nos. 4,610,655; 4,909,798 and 5,125,903. However, these hemostasis valves are generally designed for use with a particular size of medical device. Because adequate sealing around the elongated cylindrical medical devices using conventional hemostasis valves cannot be assured for a wide variety of devices, each having a different diameter, it has not been possible to utilize a single hemostasis valve with devices of widely varying diameters. Also, many of the prior art hemostasis valves exhibit various performance defects due to various structural features. For example, it may be difficult to manipulate an elongated cylindrical medical device through the passageway formed by automatically closed slits because no pre-guiding centering channel is provided. In addition, for Type I hemostasis valves, the deformation arising from the insertion of the elongated cylindrical medical device into the valve is generally in an axial direction rather than radially away from the opening. The introduction of the medical device creates an axial gap between the gaskets that may result in leakage of blood under blood pressure. For Type II hemostasis valves, such axial gaps are sometimes reduced by integrating the sealing function of two gaskets into a single gasket. With this integration the sealability seems to improve in comparison to Type I hemostasis valves. However, the insertion force necessary for insertion of medical catheters through the passageway of the valves dramatically increases because the deformation force for the two slits of the hemostasis valve is in opposition to one another and the friction at the intersecting location of the two slits inside the valves increases.

For Type III hemostasis valves, the insertion force may also be a problem. In addition, these valves often do not seal against the leakage of blood when a small-diameter guidewire passes through its slit passageway.

Further, the restitutive force created by the retraction of larger-diameter catheters may cause the seepage of air into the blood stream.

It has been recognized that axial deformation of the hemostasis valve should be limited to improve sealability. For example, U.S. Pat. No. 5,520,655 discloses a medical device wherein the valve is pre-deformed in an axial direction opposite to that of the insertion force. The axial deformation induced by the insertion of an elongated medical device is compensated for by this pre-deformation. As a result, the actual deformation during insertion seems to be radial to the valve, thus improving the sealability of the valve. However, the insertion force may increase due to this pre-deformation, and the restitutive force due to the retraction of the elongated cylindrical member may still allow the seepage of air into the blood stream.

U.S. Pat. No. 4,917,668 suggests the use of spring-loaded resilient gasket valve members with one or more spring elements augmenting the natural resilience of the sealing gasket material to improve sealability. However, the insertion force increases with incorporation of metal springs.

In yet another approach to providing a suitable seal under varying conditions encountered in practice, U.S. Pat. No. 5,125,903 discloses the use of concave and convex cusp-shaped surfaces to form the thinned central region of the valve, through which the short intersecting slits extend at a 45 degree angle to the 90 degree line of intersection.

The hemostasis valves described above represent departures from, and attempts to overcome deficiencies in, the flat-sided disk-shaped gaskets involving reduced diameter holes, slits and crossed slits therethrough to accommodate elongated cylindrical medical devices passing through the valve.

Accordingly, it is an object of the present invention to prepare a universal hemostasis valve which exhibits high performance in sealing against the leakage of blood, limiting the backflow of air into the vessels and easing insertion and retraction of elongated cylindrical medical devices of varying diameters. This hemostasis valve may be reliably used with a wide variety of both large catheters, up to about 9 F (3 mm), and small guidewires, down to 0.014 in. (0.35 mm).

It is a further object of the invention to disclose a hemostasis valve composed of a valve gasket and a separate valve membrane, wherein the valve gasket is thicker than the valve membrane.

It is a further object of the invention to disclose a hemostasis valve comprising a valve gasket and a valve membrane, wherein the valve membrane contains a positioning protrusion element which fits within a positioning slot of the valve gasket.

It is a still further object of the invention to disclose a hemostasis valve comprised of a valve gasket and a valve membrane, wherein the valve gasket contains a conical receiving area and a guiding hole to guide medical devices through the hemostasis valve.

It is a still further object of the invention to disclose a hemostasis valve, composed of a valve gasket and a valve membrane, wherein the valve membrane contains a beveled edge which interacts with a beveled edge of the valve gasket when blood pressure is placed on the hemostasis valve to convert the axial force of the blood to a radial force.

It is a still further object of the invention to disclose a hemostasis valve composed of a valve gasket and a valve membrane, wherein the valve gasket and the valve membrane maintain substantial contact against each other throughout the medical procedure.

It is a still further object of the invention to disclose a hemostasis cannula unit including a valve housing, a cap and a hemostasis valve, wherein the hemostasis valve is composed of a valve gasket and a valve membrane, wherein the valve gasket is thicker than the valve membrane.

These and other objects can be obtained by the disclosed hemostasis valve and hemostasis cannula unit which are disclosed by the present disclosure.

SUMMARY OF THE INVENTION

This invention involves a hemostasis cannula unit, which includes a longitudinally extended housing having a first and second opposing end, a cap enclosing the first end containing an opening to permit insertion of a dilator or catheter into the longitudinally extended housing, and a hemostasis valve, which consists of a valve gasket and a valve membrane compressed against the valve gasket by the valve housing, wherein the valve gasket is thicker than the valve membrane.

The invention also involves a hemostasis valve comprised of a valve gasket and a valve membrane, wherein the valve gasket is thicker than the valve membrane, and wherein an outside raised, beveled edge of the valve membrane presses against an outside depressed, beveled edge of the valve gasket when cylindrical medical devices are extended through slits in the valve membrane and gasket.

BRIEF DESCRIPTION OF THE DRAWINGS

FIG. 2 is an exploded view of the hemostasis cannula assembly showing the components thereof, including the valve gasket and the valve membrane of the hemostasis valve.

FIG. 3 is an exploded view of the hemostasis valve.

DETAILED DESCRIPTION OF INVENTION

The high performance hemostasis valve (10) of the present invention is preferably incorporated in a hemostasis cannula assembly (70) used, for example, for various cardiac catheterization procedures in which a dilation catheter or treating catheter advances over a small guidewire into a blood vessel.

Figure 1:
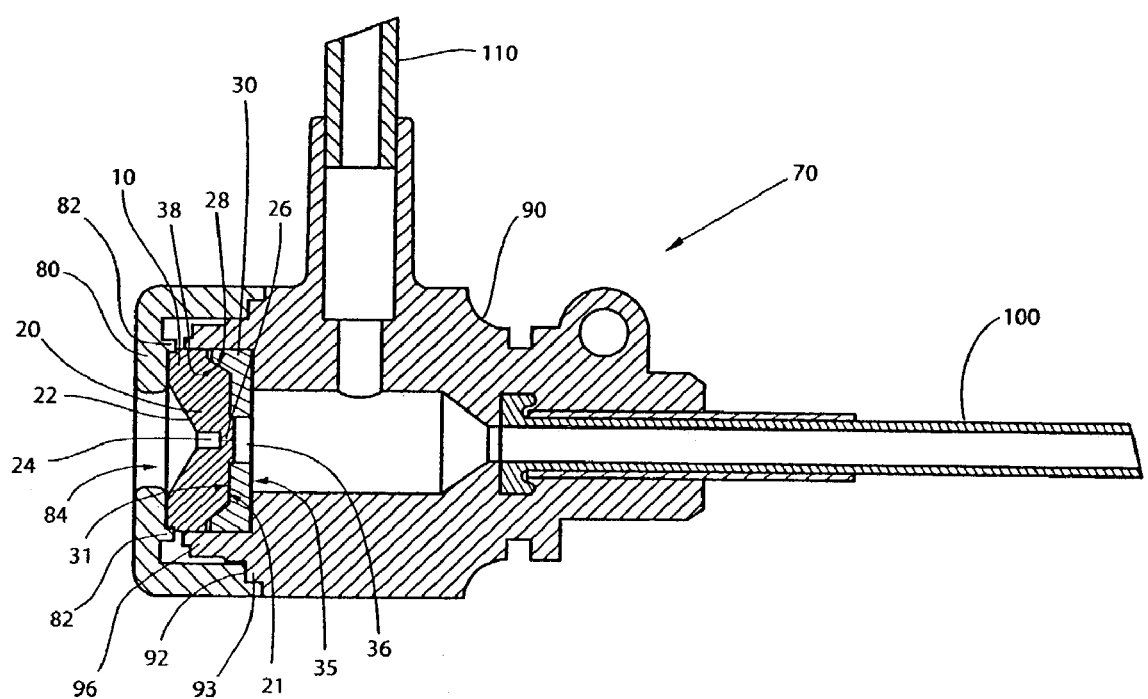
FIG. 1 is a cross-sectional view of the hemostasis valve of the present invention placed within a hemostasis cannula assembly.

The hemostasis cannula assembly (70) is formed of five major components, as shown in FIGS. 1 and 2. The first of these components is the cap (80), which is attached to the proximal end of the second component—the longitudinally extended valve housing or hub (90). The valve housing (90) has a proximal and distal opposing openings through which elongated cylindrical medical devices are inserted into and out of the interior of the valve housing or hub (90). The cap (80) and valve housing (90) of the cannula assembly (70) are preferably made from a relatively rigid thermoplastic material, such as a high-density polyethylene or an acrylonitrile-butadiene-styrene copolymer. The cap (80) may be secured to the body (96) of the valve housing (90) by mechanical means using threads, snap fittings, etc. or by gluing, but preferably it is secured by ultrasonic welding or head adhesion.

The third and fourth major components of the hemostasis cannula assembly (70) of the present invention form the hemostasis valve (10) and consist of a valve gasket (20) and a valve membrane (30) as shown in FIGS. 1,2,3 and 4. They are made from a pliant, high elastic polymeric material such as a silicon rubber, or a thermoplastic elastomer, which can readily and repeatedly permit passage of elongated cylindrical medical devices of varying diameters through the hemostasis valve (10).

The final major component of the hemostasis cannula assembly (70) of the present invention is the tubular introducer sheath (100) as shown in FIGS. 1, 2, 8 and 10, preferably made of a biocompatible thermoplastic material, such as a high density polyethylene (HDPE), polypropylene, fluoropolymer, polyether block amide (PEBA), polyamide (PA), polyvinyl chloride (PVC), polyurethane-based thermoplastic elastomer or a blend of the aforementioned polymeric materials. A multilayered tubular structure may also be used to co-extrude the introducer sheath (100) using different combinations of the aforementioned polymeric materials. The sheath (100) is inserted within the distal end of the valve housing or hub (90) and is secured in place preferably by heat adhesion or ultrasonic welding to provide an exit from the interior of the valve housing (90).

A side port (110) is preferably secured to or formed into the valve housing (90) distal to the hemostasis valve (10), as shown in FIGS. 1, 2, 8 and 10, to provide for the perfusion and aspiration of fluids through the sheath (100). The introducer sheath (100) maintains the percutaneous opening, or the access site, initially made with other devices, such as a hypodermic needle or scalpel, and provides an entrance point for a dilator or obturator, as well as the aforementioned catheters and guidewires. The introduction of the introducer sheath (100) into the blood vessel is accomplished by a dilator advancing over the guidewire, both of which are advantageously passed through the introducer sheath (100) and valve (10). Once the introducer sheath (100) is advanced a sufficient distance within the chosen blood vessel, the guidewire and dilator are removed in favor of insertion of the therapeutic catheter system, as shown, for example, in FIG. 8.

Figure 4:
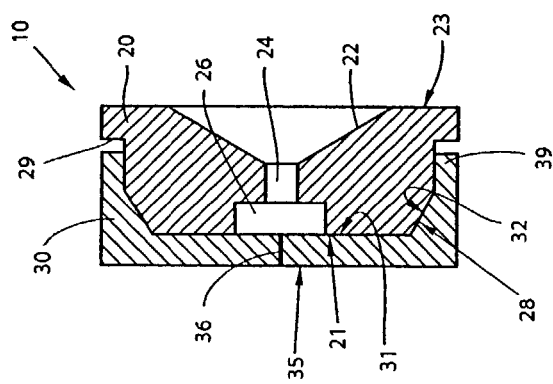
FIG. 4 is a side, cut away view of the hemostasis valve, with the valve gasket and the valve member placed together.

The valve gasket (20) and the valve membrane (30) form the hemostasis valve (10) as shown in FIGS. 1,2,3 and 4. The thicker valve gasket (20) and the thinner valve membrane (30) are assembled by aligning and inserting one or more positioning protrusions (48) of the valve membrane (30) within one or more positioning slots (50) of the valve gasket (20) as shown in FIGS. 3 and 4. The hemostasis valve (10) is inserted into the valve housing (90) at the proximal end (92) of the hub (90), as shown in FIG. 1. After assembly, a guiding cone or conical receiving area (22) of the thicker valve gasket (20) is approximately in alignment with an opening (84) through the cap (80). An inner circular section (82) of the cap (80) preferably imposes a slight axial compression of the valve gasket (20) against the valve membrane (30) after assembly of the hemostasis cannula assembly (70) as shown in FIG. 1. Preferably this pressure compresses the hemostasis valve (10) at least about 2 percent and preferably from about 2 to 5 percent within the valve housing (90).

Figure 5A:
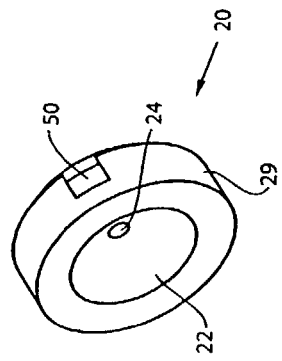
FIG. 5A is a perspective view of the valve gasket of FIG. 5.
Figure 5:
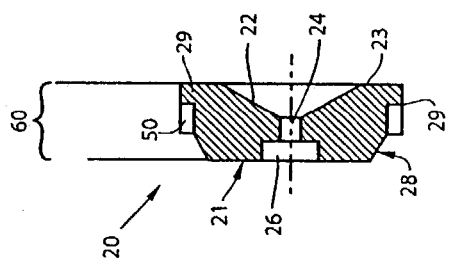
FIG. 5 is a side, cut away view of the valve gasket of the hemostasis valve with a circular guiding hole showing the thickness (60) of the valve gasket between its entry and exit faces.
Figure 6:
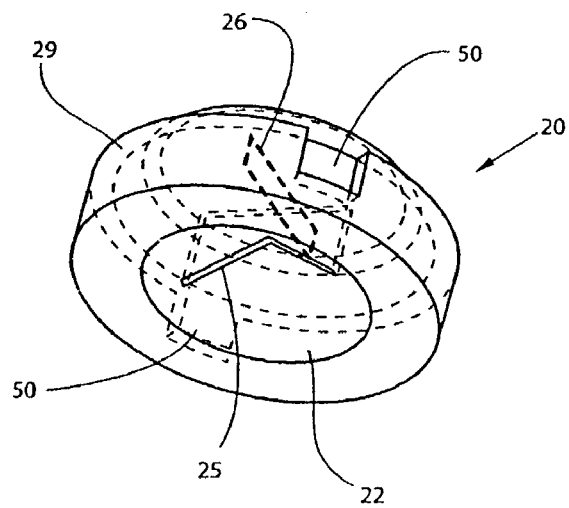
FIG. 6 is a perspective view of the valve gasket of the hemostasis valve showing a rounded edge, rectangular guiding hole and a slit.
Figure 6A:
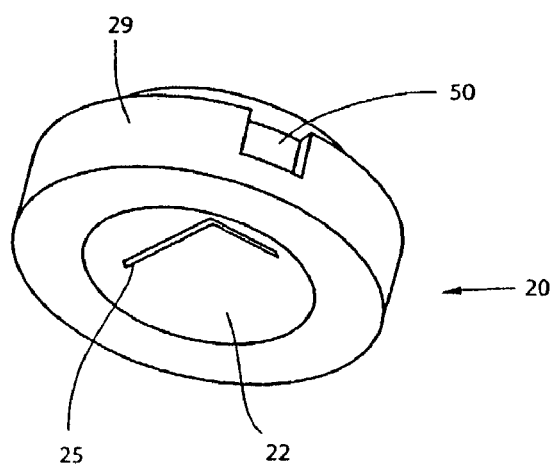
FIG. 6A is another perspective view of the valve gasket of FIG. 6.

The conical receiving area or guiding cone (22) of the valve gasket (20) tapers into the centering or guiding hole (24), as shown in FIGS. 4, 5 and 5A. The conical receiving area or guiding cone (22) tapers at an angle from about 20 to about 80 degrees, and preferably from about 20 to about 60 degrees from the outer surface (23) of the valve gasket (20). The centering hole (24) acts as a sealing neck when a catheter of larger diameter passes through the hemostasis valve (10). The centering hole (24) can be formed in any conventional cross section, either circular or non-circular. If a circular cross section is utilized as shown in FIGS. 5 and 5A, it is preferred that its diameter be that of the smallest dilator that is utilized with the hemostasis cannula assembly (70). While a circular cross section is preferred, as shown in FIGS. 5 and 5A, such as that which would accommodate a 4 French (1.33 mm) dilator, if a non-circular cross section is utilized, a rectangular cross section with rounded edges for the guiding hole (25) is preferred as shown in FIGS. 6 and 6A. The longitudinal axis of such a rectangular guiding hole (25) should be perpendicular to a slit (26) provided in the valve gasket (20). The shorter side of the rectangular guiding hole (25) should be no less than about 0.070 in. (1.8 mm) in width. The ratio of the length of this rectangular guiding hole (25) to its width is preferably from about 1.5:1 to about 10:1.

Taken together the guiding or centering hole, whether circular (24) (FIG. 5A) or rectangular (25) (FIG. 6A), and the conical receiving area (22) guide elongated medical devices to the center of the hemostasis valve (10) to permit easy insertion of a wide variety of catheters with different diameters into, and through, the hemostasis valve (10) with excellent "feel" for clinicians.

Extending distally from the guiding hole (24) of the valve gasket (20) is the slit (26) of the valve gasket (20), which entirely passes through the remaining portion of the valve gasket (20), to its exit face (21) as shown in FIGS. 1, 4 and 5. This slit (26) is preferably a single slit with its proximal edge located at the center of the guiding hole (24). The width of the slit (26) is about 0.070 in. (1.8 mm) to about 0.15 in. (3.8 mm), and preferably from about 0.09 in. (2.3 mm) to about 0.12 in. (3.0 mm). The overall thickness of the valve gasket (20) from its proximal entry face (23) through the conical receiving area (22), the guiding hole (24) and the slit (26) to its distal exit face (21) is designated by number 60 on FIG. 5.

The exit face (21) of the valve gasket (20), includes a depressed, beveled edge (28) which is angled at an angle from about 20 to about 90 degrees and preferably from about 30 to about 60 degrees from the exit face (21) of the valve gasket (20) as shown in FIGS. 4 and 5. This depressed, beveled edge (28) aligns with a corresponding raised, beveled edge (38) of the valve membrane (30) as shown in FIG. 7, so that the two components are constantly in intimate contact with each other as shown in FIG. 4. By angling the respective beveled edges (28, 38) of the valve gasket (20) and valve membrane (30) in the manner shown in FIG. 4, when an elongated cylindrical medical device is extended through the slits (26, 36) of the valve gasket (20) and valve membrane (30) respectively, the axial blood pressure acting on the hemostasis valve (10) generally converts that axial pressure to radial deformation of the valve gasket (20) stretching the valve membrane (30) about the valve gasket (20) producing a seamless pair of components, thereby producing a better "feel" for the clinician.

Figure 7A:
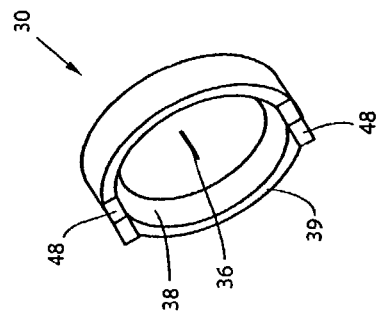
FIG. 7A is a perspective view of the valve membrane of FIG. 7.
Figure 7:
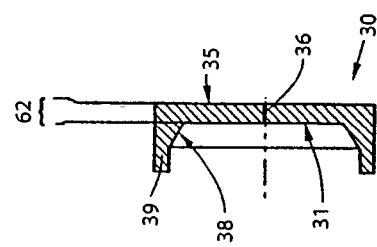
FIG. 7 is a side, cut away view of the valve membrane of the hemostasis valve showing the thickness (62) of the valve membrane between its entry and exit faces.

The second major component of the hemostasis valve (10) is the valve membrane (30), as shown in FIGS. 7 and 7A. It is designed to complement the valve gasket (20) and operate in coordination therewith to provide improved sealing for small guidewires. It is designed with a complementary shape to the shape of the valve gasket (20) such that the entry face (31) of the valve membrane (30) cooperates with the exit face (21) of the valve gasket (20), as shown in FIG. 4. Thus, the valve membrane (30) has a generally flat entry face (31) which is placed against the generally flat exit face (21) of the valve gasket (20).

The entry face (31) of the valve membrane (30) also includes the raised, beveled edge (38) of the valve membrane (30). This raised, beveled edge (38) of the valve membrane (30) is coordinated in shape with the depressed, beveled edge (28) of the valve gasket (20). It is angled with a complementary angle to the angle of the depressed, beveled edge (28) of the valve gasket (20). The outermost edge (39) of the beveled edge (38) of the valve membrane (30) preferably forms a raised portion corresponding to an outermost edge (29) of the valve gasket (20), as shown in FIG. 4. These complementary outermost edges (29, 39) assist in retaining the constant contact of the valve gasket (20) with the valve membrane (30) during medical procedures. Near the center of the valve membrane (30) is its slit (36), which is preferably placed in a perpendicular position to the position of the slit (26) of the valve gasket (20) as shown in FIGS. 3 and 6 when the valve gasket (20) and the valve membrane (30) are joined together as shown in FIG. 4. The slit (36) of the valve membrane (30) is preferably the same width as is the width of the slit (26) of the valve gasket (20). The slit (36) of the valve membrane (30) extends through the valve membrane (30) from its entry face (31) to its exit face (35), as shown in FIGS. 4 and 7. The thickness of the valve membrane (20) at this location is referenced by number 62.

It is important that the valve gasket (20) be significantly thicker than the valve membrane (30) as shown in FIG. 4. In comparing the thickness of the valve gasket (20), referenced by 60 on FIG. 5, with the thickness of the valve membrane (30) referenced by 62 on FIG. 7, the important comparison is the distance between the respective entry faces (23, 31) and the respective exit faces (21, 35) as this is the location that the medical instruments pass through the hemostasis valve (10). The thickness of the valve gasket (20) referenced by 60 is preferably from about 0.05 in (1.3 mm) to about 0.15 in (3.8 mm) while the corresponding thickness of the valve membrane (30) referenced by 62 is from about 0.02 in (0.5 mm) to about 0.05 in (1.3 mm). Preferably the thickness (62) of the valve membrane (30) is at least about 20 percent of the thickness (60) of the valve gasket (20) and more preferably from about 20 to about 75 percent of the thickness (62) of the valve gasket (20).

The cross-shaped, or mutually perpendicular, split slits (26, 36) formed by the slit (26) of the valve gasket (20) and the slit (36) of the valve membrane (30) act as the primary crisscross sealing barrier to prevent the flow of blood and air through the hemostasis valve (10). In order to assure proper alignment of the valve gasket (20) and its corresponding slit (26) with the slit (36) of the valve membrane (30), one or more positioning protrusions (48) are provided in the outer edge (39) of the valve membrane (30) which align with one or more positioning slots (50) present in the outer edge (29) of the valve gasket (20), as shown in FIGS. 3 and 4. By aligning the respective positioning protrusion(s) (48) of the valve membrane (30) with the positioning slot(s) (50) of the valve gasket (20), the respective slits (26, 36) align perpendicularly to assure proper relative position of the valve membrane (30) and the valve gasket (20) to form a crisscrossed sealing structure within the hemostasis valve (10) as shown in FIGS. 4 and 6. Obviously the placement of the positioning valve protrusions (48) on the valve membrane (30) and the positioning slots (50) on the valve gasket (20) can be reversed, if desired.

Figure 9:
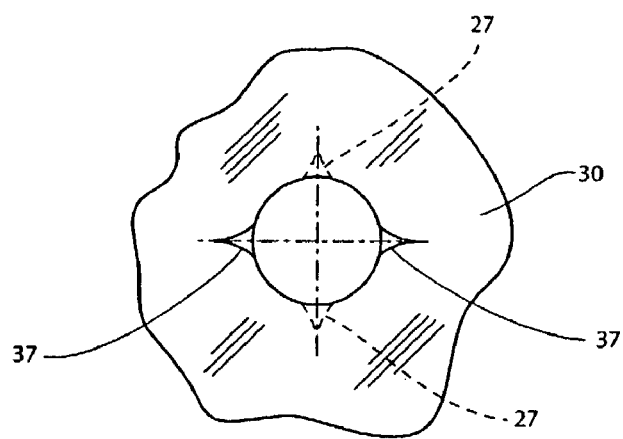
FIG. 9 is a cut away bottom view of the slit in the valve membrane of the hemostasis valve with a medical device inserted therethrough.

FIG. 9 shows a deformed configuration for the respective slits (26, 36) when an elongated cylindrical member (120) passes through the hemostasis valve (10). Two curvilinear triangle-like interstices (27, 37) are formed at the ends of the respective slits (26, 36). The interstices (27) of the valve gasket (20) and those (37) of the valve membrane (30) interweave when a cylindrical member (120) passes through the valve membrane (30) and valve gasket (20) as shown in FIG. 9. The interweaving of the interstices (27, 37) from the respective valve gasket (20) and valve membrane (30) creates a mutual barrier against the leakage of blood through the hemostasis valve (10). The leakage of blood occurs only if the two neighboring, interweaving interstices (27, 37) are connected. If the diameter of the elongated cylindrical member (120) inserted is too small, the two neighboring interstices (27, 37) remain connected, dependent on the degree of the radial compression of the hemostasis valve (10). Thus, in such cases, the leakage of blood is prevented by the initial radial compression. If the diameter of the elongated cylindrical member (120) is too large, it is possible for interweaving interstices of a conventional hemostasis valve to connect, forming a passage to prevent the leakage of blood around the circumference of the catheter. This becomes more serious when the catheter is circumferentially turned by the clinician during the insertion. However, due to the shape and structure of the valve gasket (20) and valve membrane (30) respectively of the present invention, especially the relatively thicker valve gasket (20) in relation to the relatively thinner valve membrane (30), the leakage of blood can be limited or prevented by the complimentary sealing capacity of the guiding hole (24), the diameter of which is smaller than the diameters of some large sized catheters used with the present hemostasis valve (10).

Figure 8:
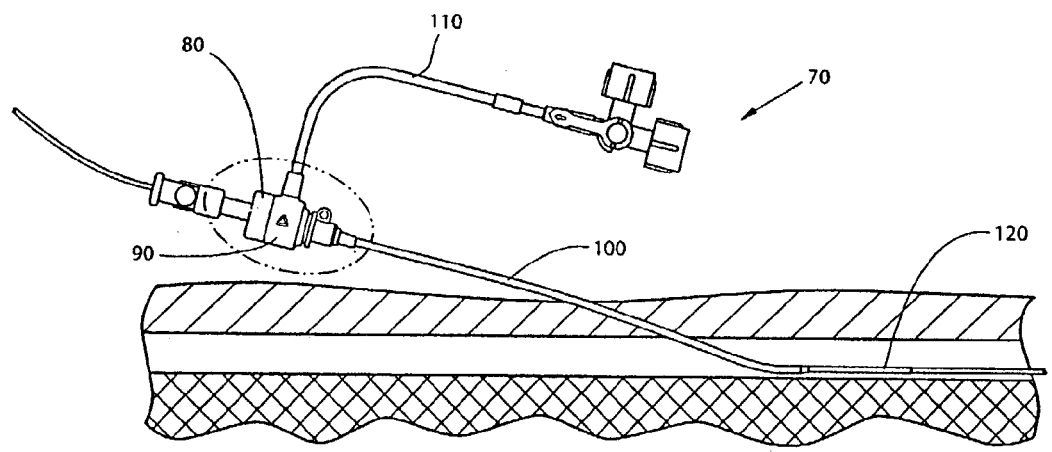
FIG. 8 is a side perspective view of the hemostasis cannula assembly of FIG. 2 inserted into the vasculature with a medical device inserted through the assembly.
Figure 10:
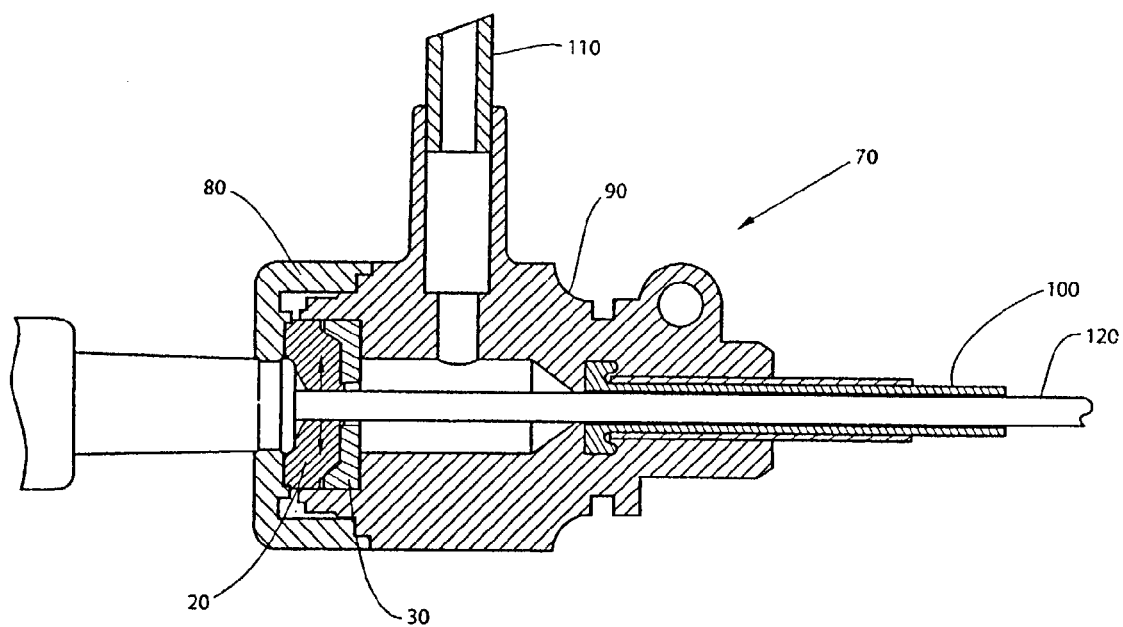
FIG. 10 is a side, cut away view of the hemostasis cannula assembly of FIG. 1 with hemostasis valve with a medical device inserted through the assembly.

When an elongated medical device (120) passes through the hemostasis valve (10) of the present invention as shown in FIGS. 8 and 10, the deformation of the valve (10) structurally self-adjusts in a radial direction from the axial direction due to the axial rigidity of the valve gasket (20) and the thinness of the valve membrane (30) in relation to the valve gasket (20). Also, during insertion the beveled edges (28, 38) of the valve gasket (20) and the valve membrane (30) respectively are pressed together as shown in FIGS. 1, 4 and 10, leading to the stretching of the valve membrane (30) in a radial direction. This stretching force, tends to reduce insertion resistance when the elongated medical device (120) passes through the valve membrane (30). However, because this radial stretching is located perpendicular to the slit (26) in the valve gasket (20), it will not affect the sealability of the hemostasis valve (10). This means the overall insertion resistance, which previously came from the friction of the medical device passing through the slits (26, 36), of the hemostasis valve (10), is reduced. The back pressure of blood acts on the exit face (35) of the valve membrane (30). Thus, due to the structural features of the present invention, including specifically the differences in relative thickness, the valve gasket (20) and the valve membrane (30) are maintained substantially in contact during the insertion of elongated medical devices, forming a seamless sealing pair with reduced insertion resistance.

When retracting a catheter during the catheterization procedure, the axially rigid structure features of the hemostasis valve (10) also self-adjust the deformation of the valve (10) primarily in a radial direction. The back pressure, along with the retracting resistant force formed by pressing the thinner valve membrane (30) tightly in contact with the exit face (21) of the thicker valve gasket (20), also self-cleans the elongated cylindrical medical device (120) while being retracted.

Due to these structural features of the hemostasis valve (10) and the difference in the thickness of the valve gasket (20) and the valve membrane (20) of the present invention, the deformations of the valve gasket (20) and valve membrane (30) are primarily in the radial direction instead of the axial direction during both insertion and retraction of the elongated cylindrical medical device. Also, because the hemostasis valve (20) occupies approximately the same amount of space in the valve housing (90) prior to, during, and after the insertion and retraction of the elongated cylindrical medical device, seepage of air into the blood stream is prevented. With the hemostasis cannula assembly (70) in place, it is possible to insert medical devices having a wide range of diameters with ease.

In use, the elongated cylindrical medical device (120) is inserted through the circular opening (84) in the cap (80) and into the hemostasis valve (10). If the medical device (120) is inserted slightly off center it will be guided by the conical receiving area or guiding cone (22) to the guiding hole (24). The medical device (120) is then advanced into the slit (26) of the axially rigid, thicker valve gasket (20) and out through the slit (36) of the axially flexible, thinner valve membrane (30). After exiting from the hemostasis valve (10), the medical device (120) is advanced through the introducer sheath (100) and into the blood vessel. Any blood which flows between the sheath (100) and the medical device (120) up into the interior of the valve housing (90) is prevented from escaping to the exterior due to the sealing action of the pair of slits (26, 36), valve gasket (20) and valve membrane (30) of the hemostasis valve (10) around the body of the medical device (120). Due to the unique structural features of the hemostasis valve (10) of the invention and the structured relationships between the relatively thicker, valve gasket (20) and the relatively thinner, valve membrane (30), resistance to insertion is reduced, and self-cleaning of blood off the medical device is provided with no seepage of air into the blood stream during retraction.

As many widely different embodiments of the present invention of the universal hemostasis valve (10) can be made without departing from the spirit, or essential characteristics, and the scope thereof, it is understood that this embodiment of the present invention is merely an illustration of the invention, and provides no limitation on its scope. Changes may be made to the specific embodiment of invention without departing from the overall invention.

We claim:

1. A hemostasis valve comprising
a valve gasket, wherein the valve gasket comprises a generally flattened disk containing a slit and a positioning slot, and
a valve membrane, wherein the valve membrane also comprises a generally flattened disk containing a slit and a positioning protrusion, wherein the positioning protrusion extends radially from a surface of the valve membrane and interacts with the positioning slot in the valve gasket when inserted into a hemostasis cannula unit, and wherein when the positioning protrusion interacts with the positioning slot, axial rotation of the valve gasket in relation to the valve membrane is prevented.

2. The hemostasis valve of claim 1 wherein the slit of the valve gasket and the slit of the valve membrane are approximately in perpendicular relationship to each other when the valve gasket and valve membrane are inserted into the hemostasis cannula unit.

3. The hemostasis valve of claim 1 wherein the valve gasket further comprises a conical receiving area.

4. The hemostasis valve of claim 3 wherein the valve gasket further comprises a centering hole located near a bottom of the conical receiving area.

5. The hemostasis valve of claim 4 wherein the centering hole is substantially circular in cross-section.

6. The hemostasis valve of claim 4 wherein the centering hole is substantially rectangular in cross-section with rounded edges.

7. The hemostasis valve of claim 6 wherein the ratio of a length to a width of the rectangular centering hole is from about 1.5:1 to about 10:1.

8. The hemostasis valve of claim 1 wherein the valve gasket further comprises a depressed, beveled portion around an outside edge of the valve gasket which interacts with a raised beveled portion around an outside edge of the valve membrane.

9. The hemostasis valve of claim 1 wherein the thickness of the valve membrane is from about 20 to about 75 percent of the thickness of the valve gasket.

10. A hemostasis valve comprising
a valve gasket, wherein the valve gasket comprises a generally flattened disk containing a slit, and a valve membrane which comprises a generally flattened disk containing a slit, wherein the valve gasket is generally thicker than the valve membrane, wherein a thickness of the valve membrane is at least about 20 percent of a thickness of the valve gasket, wherein the valve membrane further comprises a thickened portion which forms a raised ring around an outside edge of the valve membrane, wherein the valve membrane further comprises a positioning protrusion extending radially from the valve membrane and wherein the valve gasket further comprises a positioning slot which interacts with the positioning protrusion to restrict movement of the positioning protrusion when they are inserted into a hemostasis cannula unit.

11. The hemostasis valve of claim 10 wherein the slit of the valve gasket and the slit of the valve membrane are approximately in perpendicular relationship to each other when the valve gasket and valve membrane are inserted into the hemostasis cannula unit.

12. The hemostasis valve of claim 10 wherein the valve gasket further comprises a conical receiving area.

13. The hemostasis valve of claim 12 wherein the valve gasket further comprises a centering hole located near a bottom of the conical receiving area.

14. The hemostasis valve of claim 13 wherein the centering hole is substantially circular in cross-section.

15. The hemostasis valve of claim 13 wherein the centering hole is substantially rectangular cross-section with rounded edges.

16. The hemostasis valve of claim 15 wherein the ratio of a length to a width of the rectangular centering hole is from about 1.5:1 to about 10:1.

17. The hemostasis valve of claim 10 wherein the thickness of the valve membrane is from about 20 to about 75 percent of the thickness of the valve gasket.

18. A hemostasis cannula unit comprised of
a longitudinally extended valve housing having a first opening and a central longitudinal chamber communicating with a second opening;
a cap secured to the valve housing enclosing the first opening of the valve housing and providing a cap opening to permit insertion of a medical device into the first opening of the housing through the central chamber and out the second opening; and
a hemostasis valve contained within the valve housing comprising a valve gasket, wherein the valve gasket comprises a generally flattened disk containing a slit, and a valve membrane also comprising a generally flattened disk, compressed against the valve gasket by the valve housing, wherein the valve membrane further comprises a slit, wherein the valve gasket is generally thicker than the valve membrane, wherein a thickness of the valve membrane is at least about 20 percent of a thickness of the valve gasket, and wherein the valve membrane further comprises a raised beveled edge angling away from a central portion of the proximal face of the valve membrane at an angle from about 30 to about 60 degrees.

19. The hemostasis cannula unit of claim 18 wherein the cap compresses the valve gasket against the valve membrane such that an overall thickness of the valve gasket and the valve membrane is reduced at least about 2 percent.

20. The hemostasis cannula unit of claim 18 wherein the valve gasket further comprises a depressed beveled portion which interacts with the raised beveled portion of the valve membrane.

21. The hemostasis cannula unit of claim 18 wherein when a medical instrument passes through the respective slits of the valve gasket and the valve membrane, the valve gasket and the valve membrane remain substantially in contact with each other.

22. The hemostasis cannula unit of claim 18 wherein when the cap compresses the valve gasket against the valve membrane an overall thickness of the valve gasket and the valve membrane within the valve housing is reduced at least about 2 percent.

23. The hemostasis cannula unit of claim 18 wherein the thickness of the valve membrane is from about 20 to about 75 percent of the thickness of the valve gasket.

24. A hemostasis cannula unit comprised of
a longitudinally extended valve housing having a first opening and a central longitudinal chamber communicating with a second opening;
a cap secured to the valve housing enclosing the first opening of the valve housing and providing a cap opening to permit insertion of a medical device into the first opening of the housing through the central chamber and out the second opening;
a hemostasis valve contained within the valve housing comprising a valve gasket, wherein the valve gasket comprises a generally flattened disk containing a slit, and a positioning slot, and a valve membrane, wherein the valve membrane also comprises a generally flattened disk containing a slit and a positioning protrusion, wherein the positioning protrusion extends radially from a surface of the valve membrane and interacts with the positioning slot in the valve gasket when inserted into the hemostasis cannula unit, and wherein when the positioning protrusion is placed within the positioning slot, axial rotation of the valve gasket in relation to the valve membrane is prevented.

25. The hemostasis cannula unit of claim 24 wherein when a medical instrument passes through the respective slits of the valve gasket and the valve membrane, the valve gasket and the valve membrane remain substantially in contact with each other.

26. The hemostasis cannula unit of claim 24 wherein when the cap compresses the valve gasket against the valve membrane an overall thickness of the valve gasket and the valve membrane within the valve housing is reduced at least about 2 percent.

27. The hemostasis cannula unit of claim 24 wherein the thickness of the valve membrane is from about 20 to about 75 percent of the thickness of the valve gasket.

28. The hemostasis cannula unit of claim 24 wherein the valve gasket further comprises a depressed beveled portion around an outside edge of the valve gasket which interacts with a raised beveled edge of the valve membrane.

* * * * *